(12) United States Patent
Warburton

(10) Patent No.: US 6,370,940 B2
(45) Date of Patent: *Apr. 16, 2002

(54) APPARATUS FOR DETERMINING CONCENTRATION OF A GAS

(75) Inventor: P. Richard Warburton, Moon Township, PA (US)

(73) Assignee: Industrial Scientific Corporation, Oakdale, PA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/504,041

(22) Filed: Feb. 14, 2000

Related U.S. Application Data

(62) Division of application No. 09/010,189, filed on Jan. 21, 1998, now Pat. No. 6,055,840.

(51) Int. Cl.$^7$ ............................................. G01N 27/407
(52) U.S. Cl. ...................... 73/23.21; 204/424
(58) Field of Search ............................ 73/23.21, 23.24; 204/424, 425, 426

(56) References Cited

U.S. PATENT DOCUMENTS 5,310,472 A * 5/1994 Dietz et al. ................. 204/425
5,685,964 A   11/1997 Watanabe et al. ........... 204/429

FOREIGN PATENT DOCUMENTS

| EP | 744620 | * | 11/1996 |
| JP | 263458 | * | 11/1987 |
| JP | 193974 | * | 6/1996 |
| JP | 227760 | * | 8/1998 |
| JP | 235519 | * | 1/1999 |

* cited by examiner

*Primary Examiner*—Daniel S. Larkin
(74) *Attorney, Agent, or Firm*—Dennison, Scheiner & Schultz

(57) ABSTRACT

Method and apparatus for determining the concentration of an analyte gas using a gas measurement device comprising a gas sensing element having an electrical current output dependent upon concentration of a gas being measured, means for measuring the electrical output signal and means for limiting diffusion of the gas being measured to the gas measurement device and defining a path for gas being measured to enter the gas measurement device. Concentration is determined by exposing the gas sensing element to the analyte gas at a first rate of diffusion and diffusivity, and measuring the output signal for a time sufficient to establish a first steady state signal, reducing diffusion of gas to the gas sensing element to a second rate of diffusion and diffusivity, and measuring the output signal for a time sufficient to establish a second steady state signal, and calculating the concentration of the analyte gas based on the second diffusivity and the first and second steady state output signals. The method is particularly useful in calibrating gas sensors using gas source concentrations of relatively low accuracy.

11 Claims, 2 Drawing Sheets

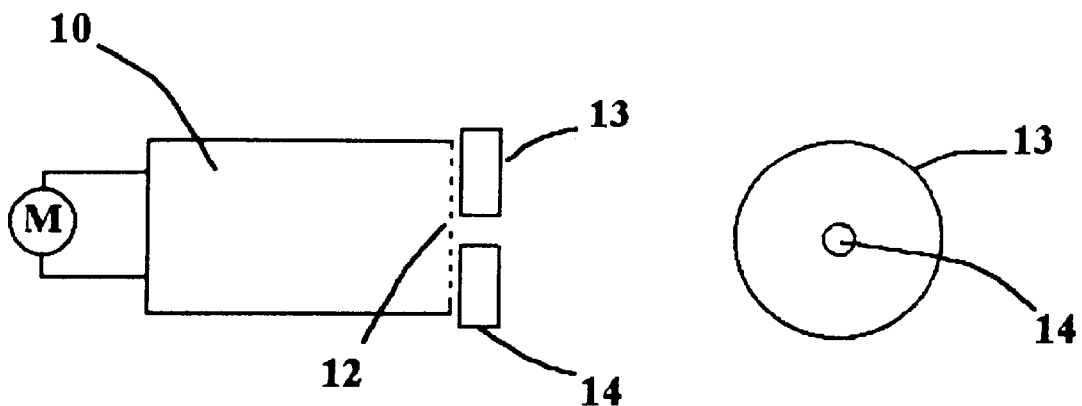
Figure 1
Figure 2
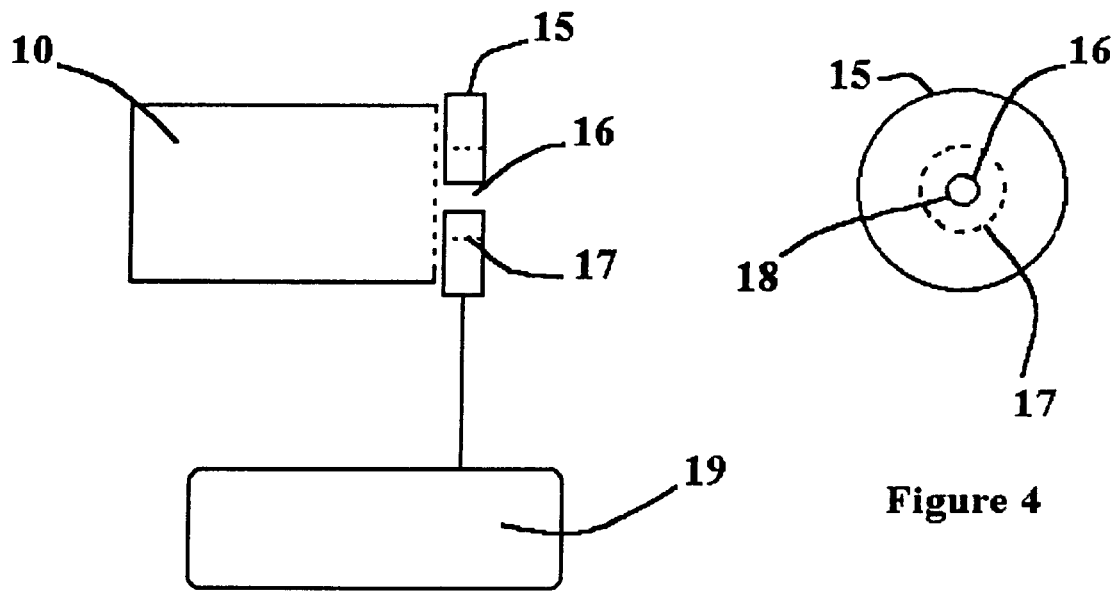
Figure 3
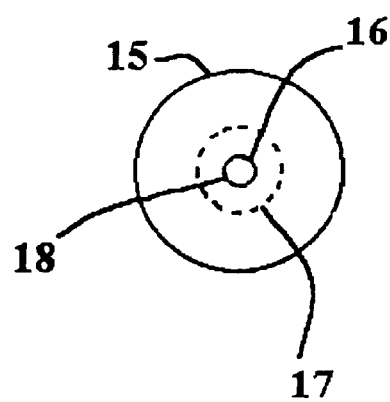
Figure 4

APPARATUS FOR DETERMINING CONCENTRATION OF A GAS

This application is a divisional of U.S. application Ser. No. 09/010,189 filed Jan. 21, 1998, now U.S. Pat. No. 6,055,840.

BACKGROUND OF THE INVENTION

1. Field of the Invention

The invention is directed to a method and apparatus for determining concentration of a gas, and particularly for calibrating a gas detection device or verifying the calibration of a diffusion limited gas detection device.

2. Description of Related Art

The technology of gas detection by means of sensors is well known in the art. There are many types of sensors available designed for various applications; one of the most common types of sensors is the diffusion limited electrochemical gas sensor. These sensors have been described, for example, in Lauer, U.S. Pat. No, 3,767,552, Oswin et al, U.S. Pat. Nos. 3,824,168, 3,909,386 and 3,992,267, and Tantram et al, U.S. Pat. Nos. 4,132,616 and 4,324,632, and are widely used for measuring oxygen concentrations in the air and for toxic gas detection for work-place safety, emission monitoring and control of pollutants, and performance optimization of combustion engines.

Most electrochemical amperometric sensors are designed such that the gas to be detected is either oxidized or reduced at an electrode within the sensor, and the gas typically passes through one or more diffusion barriers, such as a porous membrane, capillary sintered disk, etc. to reach the electrode. The majority of sensors are operated such that the response current is limited by the rate at which the gas can diffuse into the sensor. A diffusion limited sensor has the advantageous properties of a linear response to the gas concentration, stable output with small changes in operating potential due to environmental or instrumental changes (e.g. variations in power supply voltage), and either a small or at least well defined variation in output with temperature and pressure. The theory of operation and practical usage of electrochemical sensors has been discussed in detail by S. C. Chang, J. R. Stetter, C. S. Cha, Talanta, Amperometric Gas Sensors (1993), 40, 461 and by B. S. Hobbs, A.D.S. Tantram, R. Chan-Henry in *Techniques and Mechanisms in Gas Sensing*, Ed. P. T. Mosely, J. Norris, D. E. Williams, (1991).

In a typical design, a sensor will contain two or more electrodes within the sensor in contact with an ionically conductive electrolyte. One electrode is designated the sensing electrode and it is located behind a gas porous or gas permeable membrane. The gas to be detected enters the sensor and moves by diffusion through the membrane and any other diffusion barriers in the gas path to the electrode. The gas is consumed at the electrode in either an oxidation or a reduction process, and the resulting electrical charge passes from the electrode, through the external circuit to the counter electrode. The magnitude of this electric current provides the output signal. At the counter electrode, which must also be in contact with the electrolyte, an equal and opposite electrochemical reaction occurs. Thus, if entry of the gas into the sensor results in an oxidation reaction at the working electrode, then there must be an equal magnitude reduction at the counter electrode; similarly, if the gas produces a reduction at the working electrode, then there must be an equal magnitude oxidation at the counter electrode.

The output signal from an amperometric sensor in the presence of the gas to be detected is determined by the gas concentration, and by the diffusivity of the gas path through which the gas must pass to reach the sensing electrode. The diffusivity is defined here as a measure of how much gas at unit concentration will diffuse into the sensor per second, and is further defined in mathematical form below. If the diffusivity of the sensor were known, then the gas concentration could be calculated upon measuring the output current from the sensor. However, variations in the physical properties of the components used to manufacture electrochemical sensors, variations which occur during the during the operational lifetime of the sensor and the difficulties in obtaining reliable diffusion parameters for the components comprising the sensor gas path preclude this method from being used in practice.

Therefore, it is common practice for a sensor to be calibrated with a known concentration of test gas after installation into a gas detection instrument. The calibration procedure typically involves application of the test gas for sufficient time for the output signal to reach steady state, after which the instrument equates the nominal gas concentration with the output signal from the sensor. This procedure allows, for example, a instrument with a numeric display to give a visual indication of the gas concentration in common gas concentration units (e.g. $mg/m^3$, ppm, % volume). Since the output current from the sensor may vary with time, it is common practice to periodically re-calibrate the sensor; the frequency of this action is determined by the nature of the sensor and the accuracy requirements of the application. Thus for a work-pace safety application, an instrument for carbon monoxide may require calibration monthly, whereas an oxygen sensor in a medical critical care application may require more frequent calibration.

Many locations where gas detection instruments are installed are difficult to reach, or pose other problems to achieve calibration such as their locations being classified as hazardous by the National Electrical Code (NFPA 70—National Electrical Code—1996 Edition). As another example, calibration is likely to be done infrequently, if at all, in residential gas detection devices, such those introduced recently for carbon monoxide by several manufacturers, as described for example by Sneider et al. in U.S. Pat. No. 5,667,653, Stetter in U.S. Pat. No. 5,331,310 and Goldstein in U.S. Pat. Nos. 5,063,164 and 5,618,493. Even if periodic calibration of the sensor in the instrument is performed, the sensor may still fail during the time interval between calibrations, and this failure will result in false gas concentration readings, or failure to respond when exposed to the gas. Therefore, it is desirable to have a means to determine whether the output signal from the sensor is a valid measure of the gas concentration.

The problems outlined above have been addressed in the prior art to various levels of satisfaction. For example, Stetter et al in U.S. Pat. No. 4,384,925 describes a method for automatic calibration of a fixed point gas detection instrument including a calibration flow system which connects cylinders of test gas to the sensor controlled by a microprocessor. Periodically, the instrument determines if the response of the sensor is within the specified limits. Hyer and Roberts in U.S. Pat. No. 4,151,738, Hartwig and Habibi in U.S. Pat. No. 5,239,492 and Melgaard in U.S. Pat. No. 4,116,612 also describe calibration systems, where the delivery of the calibration gas to the gas detector is controlled by a microprocessor or other automated system.

Electrochemical gas generators have been used by Analytical Technology Inc. of Oaks, Pa. 19456 (8 Page Technical Information Sheet, titled *A world of gases . . . A single transmitter*) to provide test gas to automatically check the performance of gas detection instruments, and ensure that the sensors are responding within their specified limits. Finbow et al. describe in U.S. Pat. No. 5,668,302 incorporating an electrochemical gas generator within an electrochemical gas sensor, behind the diffusion barrier, to provide a means for automatic function testing of the gas detection instrument. The calibration methods though are limited by the accuracy by which the electrochemical gas generators can reliably and repetitively produce a test gas of known concentration, and in the latter example will not be able to identify a blocked gas diffusion path as being a fault.

In one example in the prior art, described by Capetanopoulos in European Patent Application No. 663,594, the response time of the sensor to a change in the external diffusion barrier was measured and the concentration of an unknown gas concentration was found by comparison to that of the response time to a change in the diffusion barrier with a known test gas concentration. However, this method, though novel, still relied upon calibration with a test gas of known concentration and involves a complex analysis based on the time response of the sensor, and so is more prone to experimental error than measuring the response at steady state.

All the methods described above rely on the presence of a test gas of known concentration. For oxygen sensors, ambient air is often used, since the concentration in well ventilated areas is a constant 20.9 volume percent; however for oxygen sensors in poorly ventilated areas and for sensors for other gases, a compressed gas cylinder or other means of producing known test gas concentrations are required to do the calibration.

A method described by Tantram and Gilbey in U.S. Pat. No. 4,829,809 does not require a known test gas concentration. A test gas of unknown concentration is passed over the sensor through a calibration flow system of known volume. After flushing the system, the gas flow is stopped and the calibration system is sealed. The output current decays to zero as the sensor consumes the gas, and the sensitivity of the initial gas concentration can be found, using Faraday's law from the integral of the current, i.e. from the total charge passed, and the volume of the sealed flow system. Waiting for the current to decay exponentially to zero is a long process and subject to errors, especially if there is a non-gas related background current, so the inventors devised a quicker analysis method involving sampling the current at various times after the start of the test, and calculating the total charge passed. This method is noteworthy because it provides a method of calibrating the sensor without requiring prior knowledge of the concentration of the test gas. However, the method is susceptible to errors due to leakage and poor mixing of the gas within the calibration flow system.

A similar system has been described by Matthiesen in U.S. Pat. No. 4,833,909 for using an electrochemical sensor to coulometrically determine a gas concentration.

Other approaches have focused on the electrical properties of the sensor. For example, Jones in U.S. Pat. No. 5,202,637 and Studer in U.S. Pat. No. 5,611,909 apply a small potential perturbation to the normally constant potential between the reference electrode and the working electrode and monitor the electrical current response of the sensor. While certainly providing a simple in-situ test that an instrument or controller can automatically perform on the sensor, this method will only detect those modes of sensor failure which affect the electrical properties of the working electrode, such as loss of volume due to dry-out from an aqueous based electrolyte. This test is unable to detect sensor faults due to problems which do not affect the electrical properties of the working electrode, for example, blockage of the gas path by dust or condensation.

Doer and Linowski have also described electrical tests for HPLC electrochemical detectors in U.S. Pat. No. 5,100,530.

SUMMARY OF THE INVENTION

Accordingly, it is an object of the invention to provide a means for calibrating a gas detection instrument, or to verify the response to gas without prior knowledge of the test gas concentration.

It is another object of the invention to provide a means for enabling calibration of a gas detection instrument using sources of gas whose concentration is known to a low degree of accuracy.

It is a further object of the invention to enable determination of the diffusion coefficient of a gas and the diffusivity of a diffusion limiting device.

To achieve these and other objects, the invention works in conjunction with gas measuring devices including a gas sensing element having a output signal response which is limited by the rate at which gas can diffuse into the sensing element. Since the output signal is limited by the rate at which gas can diffuse into the sensing element, this output signal will decrease if an additional diffusion barrier is placed in the gas path, the fractional decrease in output signal depending on the ratio of the diffusivity of the sensing element to that of the external diffusion barrier. If the diffusivity of the external diffusion barrier is known, then the diffusivity of the sensing element can be calculated by the change in response signal. Using an amperometric sensor as an example, Faraday's law can be used to calculate the concentration of the gas and the sensitivity of the sensing element can be found from the diffusivity of the sensing element and the output signal.

Accordingly, the invention provides a method for determining gas concentration and for calibration of such a gas measuring device by the steps of:

exposing the gas sensing element to a gas to be measured in a test concentration at a first rate of diffusion and diffusivity, and measuring the output signal for a time sufficient to establish a first steady state signal;

reducing diffusion of gas to the gas sensing element to a second rate of diffusion and diffusivity, and measuring the output signal for a time sufficient to establish a second steady state signal; and calculating the test concentration of the gas based on the second diffusivity and the first and second output signals.

The term "output signal" generally applies to the output current of the gas measuring device, although this will depend on the actual device used. Some amperometric devices include electronics that provide an output signal in the form of a potential difference. Catalytic bead sensors are usually operated at a constant voltage as part of a Wheatstone bridge, in which case the output signal is a change in electrical resistance, which is measured as a potential difference across the bridge. Catalytic bead sensors may also be operated at a constant temperature/power, so the output signal may be a current, a voltage or a power.

When this calculation is used for calibration purposes, subsequent measurements with the instrument are corrected based on the calculated test concentration of the gas.

The invention is further directed to the combination of a gas measurement device comprising a gas sensing element having an electrical output signal dependent upon the concentration of a gas being measured, means for measuring the electrical output signal and means for limiting diffusion of the gas being measured to the gas measurement device and defining a path for gas being measured to enter the gas measurement device, and a means in the path for selectively reducing diffusion of gas to the gas sensing element.

The invention is thus advantageous in that it permits calibration of a sensor using gas sources whose concentration is known to a lesser degree of accuracy, such as permeation tubes, electrochemical gas generators, chemical gas generators, glass ampules and gas desorption from a porous substrate. Using the method of the invention, gas concentration from such sources can be determined to a high degree of accuracy, and that concentration used to calibrate the instrument for subsequent measurements.

BRIEF DESCRIPTION OF THE DRAWINGS

FIG. 1 is a schematic view in cross section of a gas sensor and an additional diffusion barrier;

FIG. 2 is an end view of the additional diffusion barrier shown in FIG. 1;

FIG. 3 is a schematic view in cross section of a gas sensor with controllable additional diffusion barrier;

FIG. 4 is an end view of the controllable additional diffusion barrier shown in FIG. 3.

DESCRIPTION OF THE PREFERRED EMBODIMENTS

Figure 5:
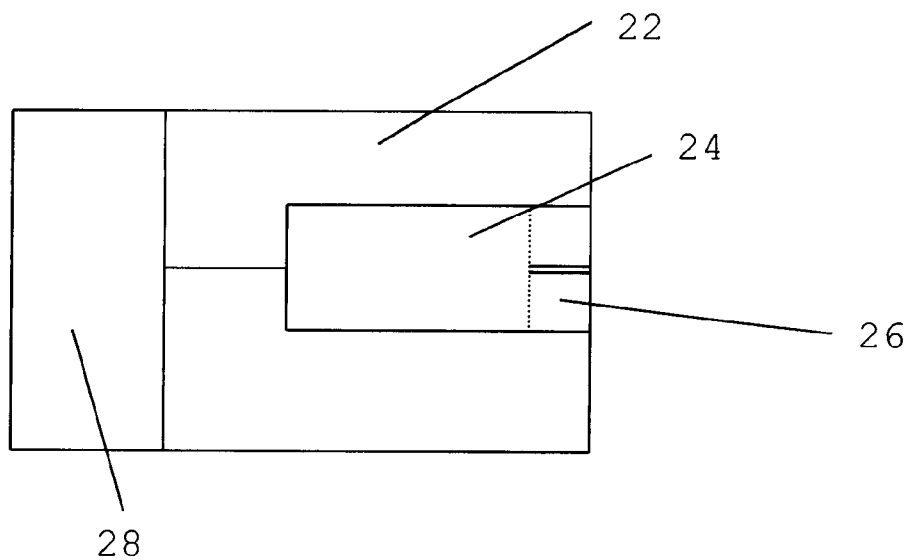
FIG. 5 is a schematic view in cross section of a housing including an apparatus of the invention.

The sensor 10 and associated electronics (not shown) in FIG. 1 are of conventional design and construction. For this discussion, it will be assumed that the sensor 10 is an amperometric electrochemical sensor, whose output current can be measured by conventional means, such as meter M, and whose steady state response to the analyte gas is limited by the rate at which the gas can enter the sensor via gas entry path 12, and travel to the electrode by diffusion. However, the use of this type of sensor is for illustrative purposes only, and it is intended that this invention be applicable to any sensor whose steady state response is limited by diffusion, and for which the output can be quantitatively related to the flux of gas reaching the sensing element.

FIG. 1 shows a sensor 10 with an additional diffusion barrier 13 in contact with the sensor, covering gas entry path 12 to the sensor. In normal use of the sensor to monitor the ambient air for the presence of the analyte gas, the diffusion barrier 13 will not be present in front of the sensor gas entry path 12.

For determining the concentration of the analyte gas, or to calibrate the sensor 10, or both, according to the invention, the following procedure may be used. The sensor 10 is exposed to an atmosphere containing the analyte gas and allowed sufficient time for the output current to reach steady state. The value of the output current from sensor 10 is recorded by conventional means and then the additional diffusion barrier 13 is placed in front of sensor 10 and in intimate contact with the gas entry path 12. The additional diffusion barrier 13 should be placed so as to make a seal against the sensor 10, so that the only path for gas to enter the sensor 10 is via the additional diffusion barrier 13. This seal may be made by conventional means, and may involve pressure, an o-ring or other means well known to those experienced in the art. The additional diffusion barrier 13 shown in FIG. 1 and FIG. 2 is a disk, with a central diffusion limiting device 14. This device may be a well defined aperture of known cross sectional area and length. The additional diffusion barrier may also be a porous membrane, gas permeable membrane, porous sintered material, air diffusion barrier, capillary, Knudsen diffusion barrier or a combination of the above means as are well known to those experienced in the art.

After the additional diffusion barrier 13 is put into place, the output from sensor 10 is again allowed sufficient time to reach steady state, and the current from sensor 10 is recorded again by conventional means. The difference between the output current of sensor 10 without the additional diffusion barrier 13 and the output current of sensor 10 with the additional diffusion barrier 13 is used to calculate the concentration of the analyte gas and the sensitivity of the sensor 10 as is described below.

Another embodiment of the invention is shown in FIGS. 3 and 4. A controllable diffusion barrier 15 is located in front of the gas entry path 12 into sensor 10. Controllable diffusion barrier 15 comprises a central diffusion limiting means, such as a variable aperture 16, which can be increased in size to aperture 17 or reduced to aperture 18, by using a control means 19. Additional diffusion barrier 15 can be left in front of the sensor 10 during normal use, with the aperture kept in the full open position 17, so as to not hinder the access of gas to the sensor 10. To measure the analyte gas concentration, or the sensitivity of the sensor 10, or both, the sensor 10 would be exposed to the analyte gas, with the aperture in the full open position 17 for sufficient time for the output current to reach a steady state. The output current from sensor 10 is then measured by conventional means, after which the aperture is reduced to diameter 18. After allowing sufficient time for the sensor 10 output current to reach steady state the current is again measured by conventional means. The analyte gas concentration and the sensor 10 sensitivity can then be calculated as described below. The aperture 16 is depicted as a circular hole for example only, and other shapes and forms of aperture, such as rectangular aperture with a sliding shutter or an elastic gas porous membrane diffusion barrier which may be subjected to varying degrees of tension to change the gas diffusion characteristics of the material, are also within the scope of this invention.

The concept behind this invention is that the steady state response of the diffusion limited sensor is determined by the analyte gas concentration and the diffusion properties of the sensor. If the diffusion properties of the sensor are known, then the concentration of the gas can be found.

For a sensor whose output is limited by the rate of diffusion, the flux of gas ω into the sensor at steady state can be described by Fick's first law of diffusion, which for a single diffusion barrier in one dimension is given by:

$$\omega = -DAdC/dx$$

where D is the diffusion coefficient for the gas, A is the cross sectional area and dC/Dx is the concentration gradient along the diffusion path. The gas diffusion path to the sensor can be considered as a series of adjacent diffusion barriers, each with a diffusivity. The diffusivity of a diffusion barrier, δ, is defined for the purposes of this invention disclosure as:

$$\delta = -DA/dx$$

and it provides a measure of how readily the gas of unit concentration will diffuse through the diffusion barrier. The diffusivity is a function of the dimensions of all the components and the diffusion coefficients of the gas through the materials comprising the diffusion barrier, and in some cases such as non-porous membranes also the solubility of the gas in these sensor components.

For most sensors, the diffusion path is not well defined, and the diffusion coefficients of the gas through the various individual diffusion barriers defining the gas path are not available, and therefore the overall diffusivity for the sensor is usually not readily calculable by this method. However, the overall diffusivity of the sensor $\delta_0$ can be calculated based on the current from the cell and the known gas concentration. If the sensor is exposed to a constant concentration of gas, C, the sensor output current $S_0$ will be determined by the relationship:

$$S_0 = \delta_0 nFC$$

where n is the number of electron and F is Faraday's constant (for electrochemical sensors only).

If an additional external diffusion barrier, with a diffusivity $\delta_1$ is placed in the gas path to the sensor, the output current from the sensor will decrease to value $S_1$, which can be described by the relationship:

$$S_1 = \delta_t nFC$$

where $\delta_t$ is the total diffusivity of the combined sensor and additional diffusion barrier. This total diffusivity can be related to the diffusivities of the sensor and the additional diffusion barrier by the equation:

$$\delta_t = \delta_0 \delta_1 / \delta_0 + \delta_1)$$

This equation is derived by assuming linear steady state conditions with zero concentration of gas at the sensing element, i.e. all the gas which reaches the electrode is consumed and the concentration of gas at the electrode is therefore zero. Substituting $\delta_t$ into the equation for $S_1$ above, and combining with the equation for $S_0$ above gives:

$$\delta_0 = (S_0 \delta_1 - S_1 \delta_1)/S_1$$

Substituting this equation into $S_0 = \delta_0 C$, above, and rearranging for C, gives a relationship between the concentration of the gas, the diffusivity of the second diffusion barrier and the current output signals of the sensor with and without the second diffusion barrier.

$$C = S_0 S_1 / (\delta_1 nF(S_0 - S_1))$$

From this equation it may be seen that it is possible to determine the absolute concentration of a gas by measuring the current output from the sensor, before and after applying an external diffusion barrier of known diffusivity. Once the test gas concentration is known, the sensor output can be calibrated to read in ppm or percent volume or any other units of gas concentration required.

In the prior art there are several examples of either variable diffusion barriers or multiple diffusion barriers being used to control the response of electrochemical sensors. For example, Mauer and Matthiessen in U.S. Pat. No. 5,092,980 describe an additional diffusion barrier to extend the concentration range of an electrochemical sensor. Cepetanopoulos in European Patent Application No. 663, 594, discussed above, uses two valves as variable diffusion barriers to calculate the concentration of gas based on the time dependence of the current signal after switching the diffusion barrier, after initial calibration with a known test gas. A third example is provided by Capetanopolous et al in U.S. Pat. No. 5,624,641, which discloses varying the diffusion barrier on an electrochemical sensor so as to control the gas concentration range for which the sensor can be used.

These examples illustrate that it is well known in the art to provide variable diffusion barriers under control of either the user or with an automatic control. Application of the external diffusion barrier and calculation of the results may be done manually, or more preferably the process may be controlled by a microprocessor or other controller. A microprocessor can also be advantageously used to analyze the calculated sensitivity from several tests, and thereby determine whether the gas concentration was constant for these tests, and thus whether the test is to be considered reliable.

In another embodiment of the invention shown in FIG. 5, the additional diffusion barrier 26 is an element of a housing 22 of the gas detection instrument which houses the sensor 24. The additional diffusion barrier can then be designed so that it presses against the sensor, and forms a seal with the edges, thus preventing gas leakage to the sensor from between the sensor and the external diffusion barrier.

The state of the external diffusion barrier, whether it be open, constricted or in another state may be under the control of the operator of the instrument or more preferably under the control of an automatic device within the instrument. An additional advantage of this embodiment is that the same additional diffusion barrier can be used, even if the gas sensor fails and is replaced by another sensor. If the diffusivity or equivalent parameter of the additional diffusion coefficient is retained by the instrument, then it can be used to calibrate the sensor when exposed to test gas, without having to know the concentration of the test gas. This information may be stored in various forms of electronic or optical memory, or data storage, or as manual or automatic adjustments to the instrument controls such as potentiometers.

The various data storage, control and calculation functions may be performed by a computer means 28 disposed in the instrument housing 22.

The concentration of the gas and the sensitivity of the sensor are calculated based on the response current of the sensor and the known diffusivity of an external diffusion barrier. The advantage of using an external diffusion barrier, which can be well defined, is that the sensor calibration is now determined by the external diffusion barrier, which is unlikely to change with time, the barrier can easily be made to well defined dimensions and thus well defined diffusion properties, and the barrier can be used repeatedly even if the sensor has to be replaced.

Another embodiment of the invention involves calibration of an instrument by the manufacturer prior to use. Even if the external diffusion barrier diffusivity is not known exactly, this invention still offers some advantages over the prior art. If a gas sensor in an instrument is exposed to test gas of known concentration with and without the external diffusion barrier, or with the external diffusion barrier in both the open and constricted positions, then the diffusivity of both the sensor and the external diffusion barrier may be calculated. If this value for the external diffusion barrier is retained by the gas detection instrument, then it can be used to calibrate the sensor at future times, or to calibrate a replacement sensor. The instrument would have to be exposed to the test gas, but the user would not have to provide the gas concentration to the instrument for the calibration to be performed. For example, many gases have short shelf lives in calibration gas cylinders, and thus the concentration of test gas may be less than the nominal value, and if this test gas were used to calibrate the gas detection instrument by conventional means, then the calibration would be in error. There are many methods available such as electrochemical gas generators or thermal methods which can generate constant concentrations of gas, but whose concentration is only approximately known, or whose concentration may vary from test to test as the electrolysis cell ages or is consumed. The use of the invention eliminates the problem of error in the calibration gas concentration found in the prior art.

Electrochemical gas generators offer the advantages of small size and less frequent maintenance compared to calibration gas cylinders. Therefore the ability to calibrate the instrument without needing to know the test gas concentration is a significant advantage over the prior art.

Figure 6:
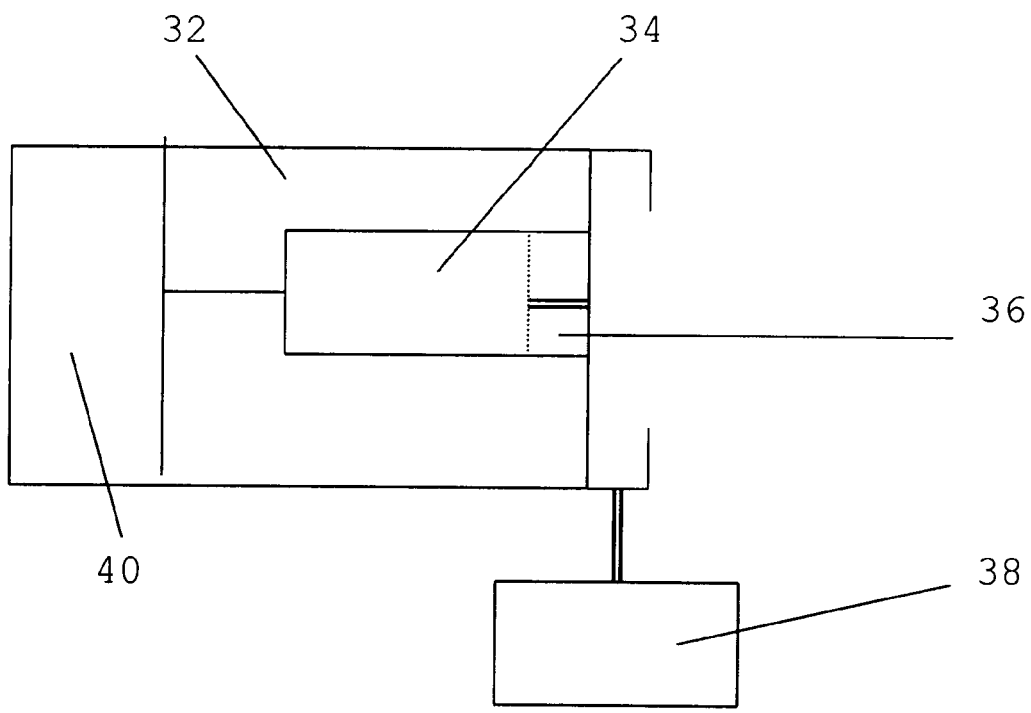
FIG. 6 is a schematic view in cross section of a housing including an apparatus of the invention in combination with a source of gas.

The instrument may include gas storage or generating means attached thereto for calibration. Thus, as shown in FIG. 6, an instrument housing 32 includes sensor 34, additional diffusion device 36, and a unit 40, which includes calculating means and data storage means. Connected to the area near the gas inlet is a gas providing means 38 which is activated for calibrating the instrument.

Another application for this invention is for use with oxygen sensors monitoring the air in confined spaces or other poorly ventilated areas, where the concentration may deviate from the ambient 20.9%. In these poorly ventilated areas, oxygen will be still present, and at an essentially constant concentration on the time scale required to apply this invention. If the sensor indicates that the concentration has deviated from the normal value, application of this invention may be used to confirm that the sensor response is indeed correct, or alternatively, even if the sensor reading is as expected, the sensor can be periodically re-calibrated using the invention. The invention will allow automatic calibration of oxygen sensors in confined spaces and other poorly ventilated areas, and with the supply of a suitable constant concentration test gas, the invention will also allow the automatic calibration of sensors for other gases as well.

It is well known in the art that the gas diffusion coefficients in air and in porous media are dependent on the temperature, and for non-Knudsen diffusion barriers, the diffusion coefficients are also dependent on the absolute gas pressure, according to well understood physical principles which has been described in detail in the literature, for example in P. W. Atkins, *Physical Chemistry*, Second Edition, W. H. Freeman & Co., San Francisco, Calif., (1982) and E. L. Cussler, *Diffusion, Mass Transfer in Fluid Systems*, Cambridge University, Cambridge, UK, (1992). Therefore, temperature compensation and pressure compensation may be used in accordance with methods well known in the art of constructing and operating gas detection devices.

The invention has so far been described for use with electrochemical sensors; however it is generally applicable to any type of sensor for which two criteria can be met. The first criterion is that the output signal is limited by the rate of diffusion into the sensor. The second criterion is that there is a quantitative relationship between the output signal and the flux of gas reaching the detection element. Thus, for example, in the diffusion limited amperometric electrochemical sensors described above, the current produced I from the oxidation or reduction of the gas to be detected can be related to the diffusional flux $\omega$ of gas by Faraday's law:

$$I=nF\omega$$

where n is the number of electrons involved in the oxidation or reduction reaction and F is the Faraday constant ($\sim 9.648 \times 10^4$ C/mol).

As another example, the responses of many catalytic bead gas sensors to combustible gases in the sub-lower explosive limit concentration range are also diffusion limited. The output signal depends on the thermal and physical properties of the sensing and reference beads, the potential difference applied to the bead, and the detection protocol. Since the output signal can be quantitatively related to the diffusional flux of the gas by matching the change in the detector bead electrical resistance with the electrical and thermal power supplied to the bead, this invention can be used with this class of gas sensors.

In the case of diffusion limited sensors, the magnitude of the output signal depends on the concentration of gas, diffusion coefficient of the gas in air and the diffusivities of the diffusion barriers for the gas traveling along the gas path into the sensor. If any two of these variables are known, the third can be calculated. Gas concentration was determined above, but the method can also be used to determine diffusivity values and diffusion coefficient.

Thus, if the sensor is exposed to a test gas, the steady state signal $S_0$ will depend on gas concentration C and diffusivity of the sensor $\delta_0$ using the equation: $S_0 = nFC\delta_0$. If the gas concentration is known, then the diffusivity $\delta_0$ of the sensor can be found from the output signal. Since the equation is written for an electrochemical sensor, it includes the number of electrons n and Faraday's constant F.

The signal decreases when the additional diffusion barrier is placed in front of the sensor to an amount $S_1$ dependent on the relative diffusivities of the sensor and additional barrier:

$$S_1 = nFC\delta_0\delta_1/(\delta_0+\delta_1)$$

If the diffusivity of either diffusion barrier is known, then the diffusivity of the other barrier can be determined without needing to know the gas concentration:

$$\delta_1 = \delta_1\delta_0/(S_0-S_1) \text{ or } \delta_0 = \delta_1(S_0-S_1)/S_1$$

If the diffusivity of the sensor is known, the diffusivity of the additional barrier can be calculated and the diffusion coefficient of the gas in a geometrically well defined gas path can be determined. For a tube of length L and cross-sectional area A, the diffusivity can is determined by Fick's first law of diffusion as $\delta_1 = DA/L$ where D is the diffusion coefficient of the gas. If $\delta_1$ is known, then the diffusion coefficient of the gas can be calculated as $D = \delta_1 L/A$.

EXAMPLE

The method of the invention was used to calibrate a commercially available three electrode electrochemical sensor for hydrogen sulfide (Riken Keiki, model ES-1537). The sensor was exposed to hydrogen sulfide diluted with zero air to a nominal concentration of 10.2 ppm volume at room temperature (23° C.). The nominal concentration of 10.2 ppm was calculated from the concentration of the source cylinder reported by the manufacturer to be 25.2 ppm and the known volume of dilution air. After allowing at least two minutes for the sensor to reach a steady state output, the output current, corresponding to $S_0$ was measured at 17.9 $\mu$A. plastic disk of thickness dx=0.318 cm, perforated with a central hole of diameter 0.16 cm and area A=0.020 cm$^2$ was placed over the sensor as a second diffusion barrier.

The sensor was again exposed to the hydrogen sulfide of nominal concentration 10.2 ppm and allowed to equilibrate; the steady state output current was measured at 3.8 $\mu$A.

Assuming a diffusion coefficient for hydrogen sulfide in air of D=0.26 cm$^2$/s, the diffusivity of the disk can be calculated by the equation $\delta_1 = DA/dx$ as $0.0164$ cm$^3$/s. The concentration C of hydrogen sulfide test gas can then be calculated from the equation $C = S_0 S_1/(\delta_1 nF(S_0 - S_1))$ as a concentration of $3.82 \times 10^{-10}$ moles/cm$^3$. At one atmosphere pressure and 23° C. temperature, the concentration can be converted by the ideal gas law to 9.3 ppm volume. The calculated hydrogen sulfide concentration thus differs from the nominal concentration by about 10%.

The error in the calculated concentration is thought to be due to the experimental error in the measurements and the uncertainty in the value in the diffusion coefficient for hydrogen sulfide. With careful design, it is thought that the experimental error can be reduced.

The foregoing description of the invention has been directed to particular preferred embodiments for purposes of explanation and illustration. It will be apparent however, to those skilled in the art that many modifications and changes in the particular design of external diffusion barrier or the number of diffusion barriers used therein as well as in the method of use may be made without departure from scope and spirit of the invention.

What is claimed is:

1. In combination, a gas measurement device comprising a gas sensing element having an electrical signal output dependent upon concentration of a gas being measured, means for measuring the electrical signal output and means for limiting diffusion of the gas being measured to the gas measurement device and defining a path for gas being measured to enter the gas measurement device, additional means in the path for selectively and reversibly reducing diffusion of gas to the gas sensing element, microprocessor means for calculating diffusivity in the gas path based on a change in the electrical signal output upon reducing diffusion in the gas path, means for storing the calculated diffusivity, and microprocessor means for correcting subsequent measurements based upon the calculated diffusivity.

2. Combination according to claim 1, wherein the means for limiting comprises a first diffusion barrier, and the means for reducing comprises a second diffusion barrier in series with the first diffusion barrier.

3. Combination according to claim 2, wherein the first and second diffusion barriers are selected from the group consisting of an orifice, an air space, a capillary element, a sintered mass, a porous membrane, a gas permeable membrane and a combination thereof.

4. Combination according to claim 1, wherein the means for limiting and the means for reducing are in the form of an orifice of variable area.

5. Combination according to claim 1, additionally comprising a housing incorporating the gas sensing element, the means for limiting and the means for reducing.

6. Combination according to claim 1, additionally comprising a microprocessor, a mechanical controller or an electrical controller for controlling the means for reducing.

7. Combination according to claim 1, wherein the gas sensing element is an amperometric electrochemical sensor.

8. Combination according to claim 1, wherein the gas sensing element is a catalytic bead sensor.

9. Combination according to claim 1, additionally comprising means for supplying a gas to be measured.

10. Combination according to claim 9, wherein the means for supplying comprises a compressed gas tank, a compressed air supply, a permeation tube, an electrochemical gas generator, a thermal gas generator or a combination thereof.

11. Combination according to claim 1, wherein the means for storage is selected from the group consisting of electronic memory, optical storage device or adjustable electronic component.

* * * * *